United States Patent [19]

Bloomfield

[11] 4,087,342
[45] May 2, 1978

[54] METHOD OF SIMULTANEOUSLY CARRYING OUT PLURALITY OF PHOTOCHEMICAL REACTIONS

[75] Inventor: Jordan J. Bloomfield, Creve Coeur, Mo.

[73] Assignee: Monsanto Company, St. Louis, Mo.

[21] Appl. No.: 753,663

[22] Filed: Dec. 22, 1976

[51] Int. Cl.² ............................ B01J 1/10; B01K 1/00
[52] U.S. Cl. ......................... 204/157.1 R; 204/158 R; 204/162 R; 204/163 R; 250/527
[58] Field of Search .................... 204/157.1 R, 158 R, 204/162 R, DIG. 11, 163 R; 250/527

[56] References Cited
U.S. PATENT DOCUMENTS

| 3,554,887 | 1/1971 | Feehs | 204/158 R |
| 3,719,454 | 3/1973 | Shang | 204/157.1 R |
| 3,993,911 | 11/1976 | Graentzel | 250/527 |

*Primary Examiner*—Howard S. Williams
*Attorney, Agent, or Firm*—Scott J. Meyer; John D. Upham

[57] ABSTRACT

A photochemical reaction system is provided in which a single polychromatic light source is used to simultaneously irradiate a plurality of photochemical reactions with different regions of the spectrum. In this system, the reactions are carried out in separate but adjacent chambers which are accessible to a single polychromatic light source and positioned in series so that each reaction provides a filter for the next adjacent reaction more remote from the light source.

5 Claims, 1 Drawing Figure

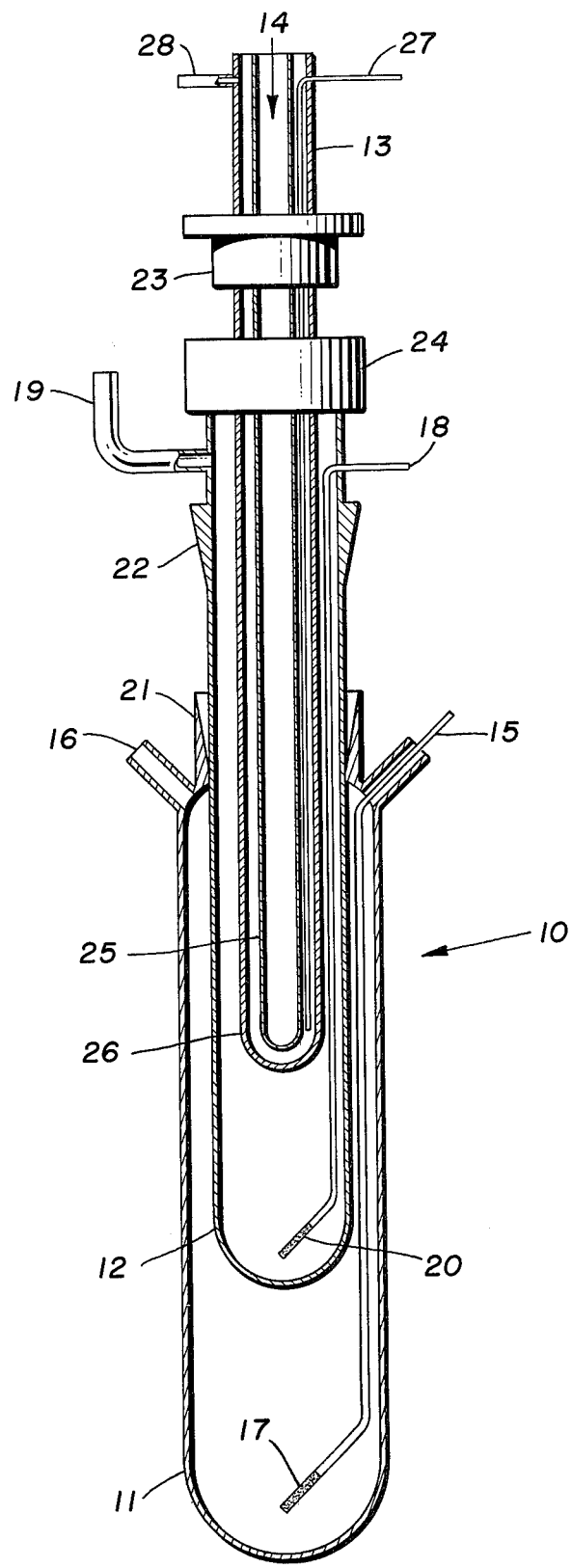

METHOD OF SIMULTANEOUSLY CARRYING OUT PLURALITY OF PHOTOCHEMICAL REACTIONS

BACKGROUND OF THE INVENTION

This invention relates to a photochemical reaction system and, more particularly, to the use of a single polychromatic light source to simultaneously irradiate a plurality of photochemical reactions with different regions of the spectrum.

The use of radiant energy such as ultraviolet light for the initiation of chemical reactions is well-known. A principal application of such use of ultraviolet light is the initiation of free radical chain reactions such as halogenation. Further background information on photochemical reaction systems can be had by reference to the following comprehensive publications:

W.A. Noyes, Jr. et al, "Advances in Photochemistry," Interscience Publ., 1963–1974;

Fitzgerald, "Analytical Photochemistry and Photochemical Analysis," Marcel Dekker Inc., 1971;

Srinivasan, "Organic Photochemical Synthesis," Wiley Interscience, 1971;

Weissberger, "Technique of Organic Chemistry", Interscience Publishers, Vol. II, "Catalytic, Photochemical and Electrolytic Reactions," 1956, Vol. XIV, "Energy Transfer and Organic Photochemistry", 1969.

A major cost of carrying out photochemical processing on a large industrial scale is electricity. This is due to the fact that conventional photochemical reactions are carried out using only part of the light spectrum at a given time. That is, any given photochemical reaction system generally utilizes only a portion of the applied spectrum and the remaining portions are left unutilized. The excess radiation may be attenuated such as by absorption or interference filtration of the unused wavelengths. While a monochromatic light source may be useful for the study of reaction mechanisms, it is difficult to obtain the high intensity required for preparative photochemical work. In the latter case, a polychromatic radiation of high intensity is generally required. Hence, a photochemical reaction system which would more effectively utilize the total applied radiant energy of a polychromatic light source would provide significant advantages over present methods of irradiation.

BRIEF SUMMARY OF THE INVENTION

In accordance with the present invention a single polychromatic light source is used to simultaneously irradiate a plurality of photochemical reactions with different regions of the spectrum. In this photochemical system, the reagents of each photochemical reaction are reacted in separate but adjacent chambers which are accessible to a single polychromatic light source and positioned in series so that each reaction provides a filter for the next adjacent reaction. Each of these reactions thus utilizes a separate region of the spectrum and from two to about four such reactions can be conveniently carried out simultaneously with a single polychromatic light source.

DETAILED DESCRIPTION OF THE INVENTION

While the specification concludes with claims particularly pointing out and distinctly claiming the subject matter regarded as forming the present invention, it is believed that the invention will be better understood from the following description taken in conjunction with the accompanying drawing in which:

The single FIGURE is an elevational view of apparatus adapted for carrying out the photochemical reaction system of the present invention.

Referring now to the FIGURE, reference numeral 10 refers generally to a photolysis reactor which is adapted for carrying out two photochemical reactions simultaneously with a single polychromatic light source. Reactor 10 comprises an outer reaction chamber 11, an inner reaction chamber 12, and a quartz immersion well 13. Reaction chambers 11 and 12 and immersion well 13 are seen to comprise a series of concentric cylinders or tubes nested one inside the other. Reaction chambers 11 and 12 thus are each adapted to hold the reactants for a given photochemical reaction while immersion well 13 is adapted to hold internally a polychromatic light source 14 such as, for example, a mercury vapor arc. Because of its light transmittance properties, quartz is the preferred material for construction of the immersion well.

In order to carry out more than two photochemical reactions simultaneously, for example 3 or 4 reactions, reactor 10 can be equipped with, respectively, one or two additional reaction chambers which can be similar to reaction chambers 11 and 12 and positioned in concentric relationship thereto.

Each reaction chamber is provided with gas supply means. Thus, chamber 11 has gas inlet 15, gas outlet 16 and fritted disc 17 for diffusion of gas through the chamber. Similarly, chamber 12 is provided with gas inlet 18, gas outlet 19 and fritted disc 20. These gas supply means can be used for supplying reactant gases or for purging the reaction chambers with nitrogen.

Reaction chamber 12 is shown to be adapted for seating on reaction chamber 11 at ground joints 21 and 22 while immersion well 13 is shown to be adapted for mating to reaction chamber 12 with a coupling means comprising male part 23 and female part 24. Other suitable seating means or coupling means can be used interchangeably between the concentric tubes but use of a threaded coupling means advantageously provides for controlled lowering of a mercury vapor arc into the inner reaction chamber to any desired depth.

Immersion well 13 is a double walled well having inner wall 25 and outer wall 26 to serve as a cooling water jacket and is provided with cooling water inlet 27 and outlet 28 for the circulation of cooling water to protect the solution to be photolyzed from the heat of the light source 14.

Most photochemical reactions are initiated with wavelengths in the visible and ultraviolet regions. For such photochemical reactions, the preferred source of radiant energy used in the present invention is a mercury vapor arc. A mercury arc consists essentially of an electrical discharge through mercury vapor at an appropriate pressure. Mercury vapor arcs are of a low, medium or high pressure. Each type emits a characteristic spectrum and intensity and, thus, has specific applications for photochemistry. In general, medium- and high- pressure mercury vapor arcs having a broad spectral output which extends over the range 200–600 nm are particularly useful in the present invention. Medium pressure arcs generally have a pressure of a few atmospheres while high pressure arcs extend upward to 100 atmospheres.

Since the rate of reaction in photolysis is directly proportional to the source intensity, a source intensity should be used to bring about the desired conversion in a convenient time interval. A variety of well-known mercury vapor arcs are available commercially to satisfy these needs. A Hanovia Type L, 679A, 450 watt lamp with the following spectral distribution is representative of a suitable medium pressure mercury vapor arc.

| Mercury Line, A | Radiated Watts |
|---|---|
| 2482 | 2.3 |
| 2537 | 5.8 |
| 2652 | 4.0 |
| 2804 | 2.4 |
| 2967 | 4.3 |
| 3025 | 7.2 |
| 3130 | 13.2 |
| 3341 | 2.4 |
| 3660 | 25.6 |
| 4045 | 11.0 |
| 4358 | 20.2 |
| 5461 | 24.5 |
| 5780 | 20.0 |

The following examples will further illustrate the invention although it will be understood that the invention is not limited to these specific examples.

EXAMPLE 1

The photochemical reaction system of this invention is illustrated by the simultaneous irradiation of two photochemical reactions, each of which utilizes a different region of the light spectrum. The first photochemical reaction consists in reacting cyclohexene-1,2-dicarboxylic acid anhydride with ethylene to yield bicyclo[4.2.0]octane-1,6-dicarboxylic acid anhydride:

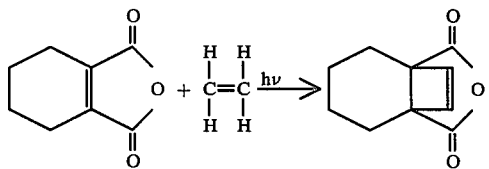
I.

The second photochemical reaction consists in reacting isophorone with cyclopentene to yield 5,5,7-trimethyltricyclo[6.3.0.0$^{2,7}$]undecane-3-one:

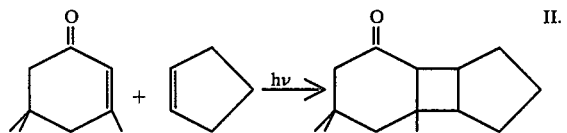
II.

The photochemical synthesis carried out in reaction I uses the spectral region 2537-2753 A while the synthesis in reaction II uses light of wavelengths 2804-3341 A. Thus, the photolysis reaction I at 2537-2753 A acts as a filter solution for reaction II at 2804-3341 A.

The foregoing two reactions were carried out in a photolysis reactor similar to that shown in the FIGURE using a quartz immersion well and a Pyrex ® glass inner reaction flask. To the inner photolysis reaction flask 12 was added 152 grams (one mole) of sublimed cyclohexene anhydride dissolved in one liter of ethyl acetate. The ethylene flow through gas inlet tube 18 was adjusted to 50 ml/minute. The outer photolysis reaction flask 11 was filled with 2 liters of a methylene chloride solution containing 138 g (one mole) of isophorone and 140 g (2 moles) of cyclopentene and the nitrogen flow through gas inlet tube 15 was set at 0.5 liter/minute.

The entire apparatus was immersed in a circulating cold water bath in a hood. The water cooled quartz immersion well 13 contained a 450 watt Hanovia lamp which was turned on after 0.5 hour. The reactions were monitored on a Varian 1200 FID gas chromatograph with a 3.1 m × 3 mm, 1% OV-210 (trifluoropropyl methyl silicone) on 100/120 Chromosorb G(HP) column programmed from 100° to 260° at 20°/minute.

A sticky brown residue was removed from the quartz immersion well 13 after 17 hours and again after additional periods of 13 and 11 hours. After a total irradiation period of 45.5 hours the cyclohexene anhydride was entirely consumed. The solution in the inner flask was removed by suction through the gas inlet tube and the flask was rinsed thoroughly with 5-100 ml portions of methylene chloride which were added to the original contents. Then, 152 g of cyclohexene anhydride (crystallized) in one liter of methylene chloride was placed in the inner flask and 70 grams of cyclopentene was added to the outer flask. Irradiation was continued for 61 hours at which point some isophorone was still present in the outer flask while all the starting anhydride in the inner flask was used up.

The solutions were separately stripped of solvent and then independently distilled through a 10 inch length vacuum jacketed Vigreaux column fitted with a variable take-off head. The first batch of the bicyclic anhydride product of reaction I was distilled at 128°-131°/4 mm to give 141.0 g (78.3%) leaving a pot residue of 23 g. The second batch of anhydride was distilled at 4 mm to give a forerun, bp 70°-128° C, 2.8g, and the product, bp 128°-131°/4 mm, 151.6 g (84.2%) and leaving a pot residue of 8.6g.

The ketone product of reaction II was distilled at 0.2 mm and collected in four fractions: (a) 35° C, 21.7 g (15.7% recovered isophorone); (b) 35°-73° C, 3.9 g (isophorone and product); (c) 73° C, 123.6 g; and (d) 71°-73° C, 38.2 g. Fractions (c) and (d) were both mixtures of two major components representing different isomers of 5,5,7-trimethyltricyclo[6.3.0.0$^{2,7}$]undecane-3-one in 92.3% yield based on unrecovered isophorone.

EXAMPLE 2

The photochemical reaction system of this invention is illustrated by another dual irradiation in which the inner flask reaction is the same as in Example 1, but in which the photochemical reaction in the outer flask consists in reacting isophorone with vinyl acetate to yield 4,4,6-trimethyl bicyclo[4.2.0]octane-2-one (7 or 8) acetate:

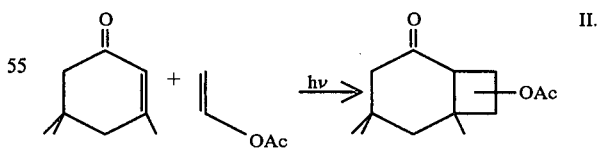
II.

Cyclohexene anhydride, 152 g (one mole dissolved in one liter of methylene chloride was placed in the inner flask of the multireaction apparatus and the ethylene flow was adjusted to 40-60 ml/minute. The outer flask was filled with two liters of methylene chloride solution containing 69 g (0.5 mole) of isophorone and 108 g (1.25 moles) of vinyl acetate with a nitrogen flow rate of 0.5 liter/minute. The water cooled quartz immersion well contained a Vycor ® filter and a 450 watt Hanovia lamp. The whole apparatus was immersed in a circulating cold water bath. After 32.3 hours, GLC on a 3.1 m × 3 mm 1% OV-210 column programmed from 100° to 260° at 20°/minute showed that the starting anhydride was completely used up. The solution was removed by suction from the inner flask, the solvent was stripped therefrom and the residue was dissolved in 400 ml of a hot 50:50 mixture of cyclohexane and benzene. The filtered solution was cooled to give a first crop of anhydride, 132.7 g (73.7%). Cooling of the solution −5° C gave an additional 27.8 g (15.4%). Concentration of the solution gave a sticky solid, 17.4 g, which was greater than 95% of the desired product of reaction I, for an overall yield of 98%. The last fraction is most readily purified by combining with the dregs of other runs and distilling.

The irradiation of the ketone of reaction II was continued for another 18 hours for a total irradiation time of 50.3 hours. At this point, although some isophorone remained, the solvent was stripped and the product distilled at 0.2 mm to give five fractions; (1) bp 34°–60° C, 10.5 g (mainly > 90% isophorone); (2) bp 78°–83° C, 2.9 g (mixture of acetate containing about 15% lower boilers); (3) bp 83°–88° C, 12.8 g (> 95% acetate mixture; (4) bp 88°–89° C, 41 g; (5) bp 90°–93° C, 22.9 g. The last two fractions and most of fraction 3 represent a yield of 80.2% of a mixture of three isomeric 4,4,6-trimethyl bicyclo[4.2.0]octane-2-one (7 or 8) acetates based on unrecovered isophorone. A viscous pot residue of 12.0 grams remain after the distillation.

EXAMPLE 3

The photochemical reaction system of Example 1 is expanded to include a third photochemical reaction which utilizes the visible light region of the spectrum by adding a third, outer reaction chamber in concentric relationship to the other two reaction chambers. The third reaction, which utilizes the visible region, consists of the photochlorination of toluene to benzyl chloride:

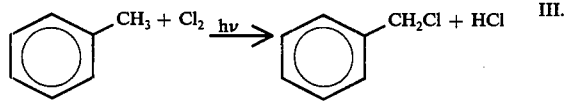

Reaction III is carried out simultaneously with reactions I and II of Example 1 and the photochemical reaction system thereby utilizes three regions of the spectrum.

EXAMPLE 4

In a similar manner to Example 3, a fourth photochemical reaction is carried on simultaneously with reactions I, II and III to utilize the 3660 A region of the spectrum in a fourth concentric tube.

Other suitable examples of photolytic reactions which can be carried out in the photochemical reaction system of this invention are:

1. The photolysis of dimethyl acetylenedicarboxylate and ethylene to dimethyl 1,5-hexadiene-2,5-dicarboxylate as disclosed in U.S. Pat. No. 3,803,215; and
2. The photocycloaddition of 2,5-dihydrothiophene 1,1-dioxide and maleic anhydride to 3-thiabicyclo(3.2.0) heptane-6,7-dicarboxylic anhydride 3,3-dioxide as described in U.S. Pat. No. 3,873,568.

Still other examples of suitable photolytic reactions will be readily apparent to the person skilled in the art. The photolytic reactions employed should be such as to selectively utilize the respective spectral regions of interest.

It will be appreciated that the invention is not limited to the specific apparatus described herein, such description being for illustrative purposes only. Thus, instead of an internal immersion light source, an external light source can be used. In the latter system, the light source is placed outside the photolysis reactor, and preferably is disposed circumferentially about the reactor with the light being directed toward the reaction chambers from all sides. In such system, reaction I of Example 1 would be carried out in the outer reaction chamber instead of the inner chamber and reaction II would be carried out in the inner chamber. The outer reaction chamber would then have a quartz wall and there would be no need for the quartz immersion well.

Continuous flow reactors also can be employed for large scale use in which suitable inlet and outlet means, pumping and valving means can be included in the photolysis apparatus for carrying reactants and products to and from the reactor.

Various other examples will be apparent to the person skilled in the art after reading the foregoing description without departing from the spirit and scope of the invention and it is intended that all such further examples be included within the scope of the appended claims.

What is claimed is:
1. A method of carrying out photolysis comprising simultaneously irradiating a plurality of photochemical reactions in which said reactions are carried out in separate reaction chambers adjacent to each other in a series and accessible to a single polychromatic light source whereby each said reaction utilizes a different region of the light spectrum and provides a filter for the next adjacent reaction more remote from the light source.
2. The method of claim 1 in which the adjacent series of reaction chambers comprises a concentric series of cylinders.
3. The method of claim 1 in which the adjacent series of reaction chambers comprises a concentric series of cylinders and in which the light source is applied from an internally disposed immersion well.
4. The method of claim 3 in which the light source is a mercury vapor arc.
5. The method of claim 1 in which the light source is a mercury vapor arc.

* * * * *